(12) United States Patent
Shimojo et al.

(10) Patent No.: US 10,494,329 B2
(45) Date of Patent: Dec. 3, 2019

(54) METHOD FOR SYNTHESIZING TETRAALKYLNITRILOACETIC ACID DIACETAMIDE COMPOUND

(71) Applicant: JAPAN ATOMIC ENERGY AGENCY, Ibaraki (JP)

(72) Inventors: Kojiro Shimojo, Ibaraki (JP); Hirochika Naganawa, Ibaraki (JP)

(73) Assignee: JAPAN ATOMIC ENERGY AGENCY, Ibaraki (JP)

( * ) Notice: Subject to any disclaimer, the term of this patent is extended or adjusted under 35 U.S.C. 154(b) by 0 days.

(21) Appl. No.: 16/131,479

(22) Filed: Sep. 14, 2018

(65) Prior Publication Data

US 2019/0092718 A1    Mar. 28, 2019

(30) Foreign Application Priority Data

Sep. 22, 2017    (JP) .................................. 2017-182484

(51) Int. Cl.
  *C07C 231/02*    (2006.01)
(52) U.S. Cl.
  CPC .................................. *C07C 231/02* (2013.01)
(58) Field of Classification Search
  CPC .................................................. C07C 231/02
  See application file for complete search history.

(56) References Cited

U.S. PATENT DOCUMENTS 3,621,018 A * 11/1971 Hindersinn .......... C07D 265/32
                                              528/114
5,201,998 A     4/1993 Töpfl et al.

FOREIGN PATENT DOCUMENTS

| JP | 2017-95407 | 6/2017 |
| JP | 2017-95768 | 6/2017 |
| JP | 2017-95774 | 6/2017 |

OTHER PUBLICATIONS

Belgian Search Report dated Mar. 21, 2019 in corresponding Belgian Patent Application No. 2018/5628.

* cited by examiner

*Primary Examiner* — Rosalynd A Keys
(74) *Attorney, Agent, or Firm* — Wenderoth, Lind & Ponack, L.L.P.

(57) ABSTRACT

In synthesis of a compound represented by the General Formula (1) or a salt thereof, nitrilotriacetic acid as its raw material is reacted with a dehydrating agent to allow dehydration, and the resulting nitrilotriacetic acid anhydride is reacted with a dialkylamine to obtain a reaction intermediate product. The reaction intermediate product is then similarly reacted with a dehydrating agent to allow dehydration, and the resulting reaction intermediate anhydride is reacted with a dialkylamine to synthesize a tetraalkylnitriloacetic acid diacetamide compound.

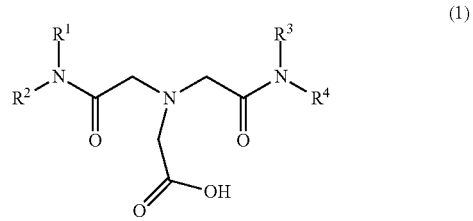

(1)

In Formula (1), $R^1$, $R^2$, $R^3$ and $R^4$ independently represent the same or different hydrocarbon group, with the proviso that the total number of carbon atoms in the hydrocarbon groups $R^1$, $R^2$, $R^3$, and $R^4$ is 8 to 64.

12 Claims, 1 Drawing Sheet

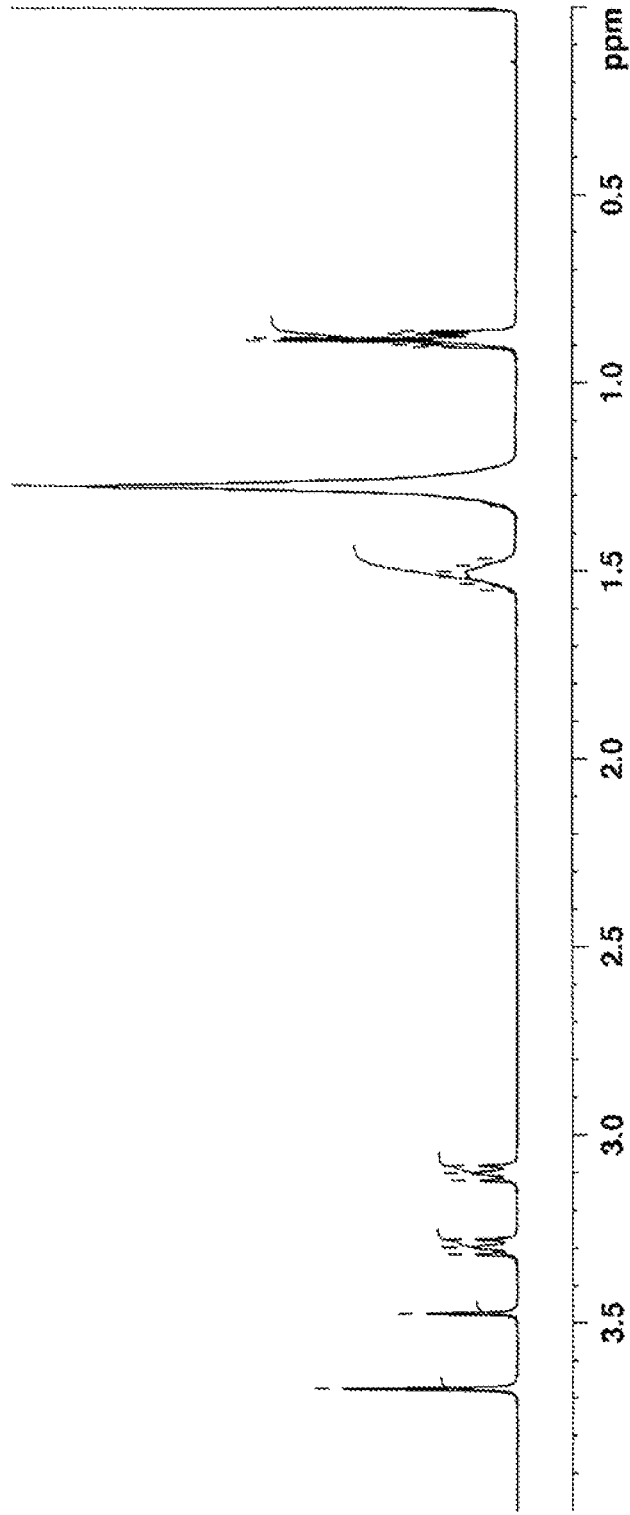

METHOD FOR SYNTHESIZING TETRAALKYLNITRILOACETIC ACID DIACETAMIDE COMPOUND

TECHNICAL FIELD

The present invention relates to a method for synthesizing a tetralkylnitriloacetic acid diacetamide compound.

BACKGROUND ART

Valuable metals such as rare metals and noble metals are used in a wide range of industrial fields, and it is very important for Japan, where resources are poor, to stably secure valuable metals.

A major method for separation, recovery, and purification of valuable metals is solvent extraction. Solvent extraction uses an industrial extractant such as a phosphoric acid-based extractant, carboxylic acid-based extractant, or oxime-based extractant. Known representative examples of phosphoric acid based extractants include a di(2-ethylhexyl) phosphoric acid and its analog 2-ethylhexylphosphonic acid mono-2-ethylhexyl ester; known representative examples of carboxylic acid-based extractants include neodecanoic acid; and known representative examples of oxime-based extractants include 2-hydroxy-5-nonylacetophenone oxime and 5,8-diethyl-7-hydroxy-6-dodecaoxime.

Further, the present inventors recently discovered that particular tetraalkylnitriloacetic acid diacetamide compounds and salts thereof are very preferable as extractants for extraction of metallic elements (see, for example, Patent Documents 1, 2, and 3). However, the synthesis methods for these extractants are complicated, and their production costs are high. Therefore, at present, the cost performances of these methods are rather poor.

Known examples of synthesis methods for tetraalkylnitriloacetic acid diacetamide compounds include a production method including the following Steps (a) to (c):

(a) a step of performing nucleophilic substitution reaction of a dialkylamine with a 2-halogenated acetyl halide to obtain a 2-halogeno-N,N-dialkylacetamide;

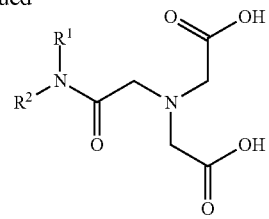

(b) a step of performing nucleophilic substitution reaction of iminodiacetic acid with the 2-halogeno-N,N-dialkylacetamide to obtain a nitrilotriacetic acid derivative;

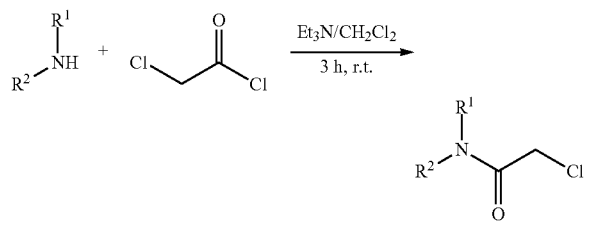

(c) a step of performing amidation of one carboxyl group of the nitrilotriacetic acid derivative with a dialkylamine to obtain a tetraalkylnitriloacetic acid diacetamide compound;

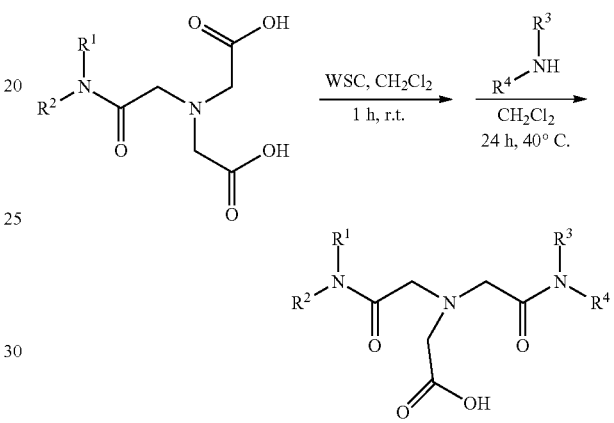

wherein $R^1$, $R^2$, $R^3$ and $R^4$ independently represent the same or different hydrocarbon group, with the proviso that the total number of carbon atoms in the hydrocarbon groups $R^1$, $R^2$, $R^3$, and $R^4$ is 8 to 64.

Dichloromethane, which is used as a reaction solvent in this synthesis method, is designated as a harmful substance in the Act on the Evaluation of Chemical Substances and Regulation of Their Manufacture, etc.; Industrial Safety and Health Act; Air Pollution Control Act: Water Pollution Prevention Act; PRTR Law; and the like, and its use should be avoided. Further, chloroacetyl chloride is designated as a non-medical deleterious substance. Because of extremely high reactivity, it is highly irritative and corrosive. Chloroacetyl chloride drastically reacts with water to cause strong production of heat, and also production of hydrogen chloride. Therefore, its use should be avoided. Further, since a condensing agent water-soluble carbodiimide (WSC) is an expensive chemical, the production cost of tetraalkylnitriloacetic acid diacetamide synthesized using it as a raw material is high. This indicates that, while the efficiency of the extraction separation step using this compound can be increased due to excellent extraction separation performance, the metal extractant cost is high, so that the overall cost cannot be reduced.

PRIOR ART DOCUMENTS

Patent Documents

[Patent Document 1] JP 2017-95497 A
[Patent Document 2] JP 2017-95774 A
[Patent Document 3] JP 2017-95765 A

SUMMARY OF THE INVENTION

An object of the present invention is to provide a method for synthesizing a tetraalkylnitriloacetic acid diacetamide compound that can be used as an extractant for extraction of a valuable metal such as a rare metal or a noble metal, or of a highly toxic, harmful metal, which, enables simple, safe, and low-cost production of the compound without use of a hazardous chemical or an expensive chemical.

In order to solve the above problems, the present inventors intensively studied and found that a tetraalkylnitriloacetic acid diacetamide compound can be synthesized by reacting nitrilotriacetic acid as a raw material with a dehydrating agent to allow dehydration, evaporating unreacted dehydrating agent and its reaction residue under reduced pressure, reacting the resulting nitrilotriacetic acid anhydride with a dialkylamine to obtain a reaction intermediate product, similarly reacting the reaction intermediate product with a dehydrating agent to allow dehydration, evaporating unreacted dehydrating agent and its reaction residue under reduced pressure, and then reacting the resulting reaction intermediate anhydride with a dialkylamine to synthesize the tetraalkylnitriloacetic acid diacetamide compound. The present inventors thereby found that this method can be simply carried out at low cost.

The present invention thus provides a method for synthesizing a compound represented by the General Formula (1):

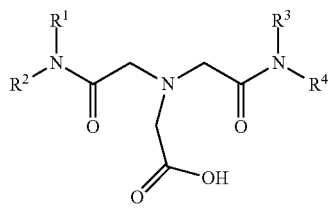

(1)

wherein in Formula (1), and $R^1$, $R^2$, $R^3$, and $R^4$ each represent the same or different hydrocarbon group, with the proviso that the total number of carbon atoms in the hydrocarbon groups $R^1$, $R^2$, $R^3$, and $R^4$ is 8 to 64, the method comprising the following Steps (I) and (II):

Step (I): dehydrating (intramolecularly esterifying) nitritotriacetic acid (i) to obtain nitrilotriacetic acid anhydride (ii), and reacting the nitrilotriacetic acid anhydride (ii) with a dialkylamine $NHR^1R^2$ to obtain a nitrilotriacetic acid derivative (iii);

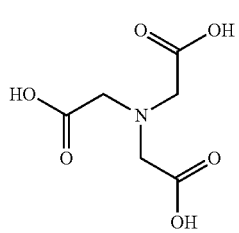

(i)

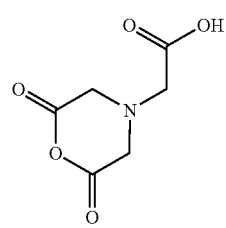

(ii)

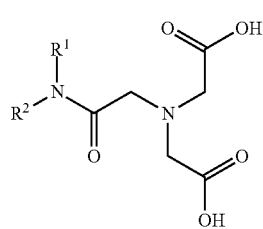

(iii)

and

Step II): dehydrating (intramolecularly esterifying) the nitrilotriacetic acid derivative (iii) to obtain a nitrilotriacetic acid derivative anhydride (iv), and reacting the nitrilotriacetic acid derivative anhydride (iv) with a dialkylamine $NFR^3R^4$ to obtain the compound represented by General Formula (1).

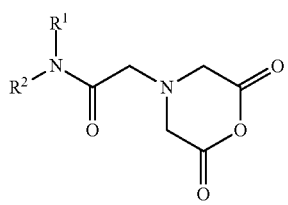

(iv)

According to the present invention, a method for synthesizing a tetraalkylnitritoacetic acid diacetamide compound that can be used as an extractant for extraction of a valuable metal such as a rare metal or a noble metal, or of a highly toxic, harmful metal, which enables simple, safe, and low-cost production of the compound without use of a hazardous chemical or an expensive chemical, is provided. The present invention is therefore industrially highly useful.

BRIEF DESCRIPTION OF THE DRAWINGS

The drawing is a diagram showing a $^1H$ NMR spectrum of tetraotylnitriloacetic acid diacetamide (TONTADA) synthesized in Example 1.

EMBODIMENTS FOR CARRYING OUT THE INVENTION

The present invention is described below by referring to some embodiments. The present invention, however, is not limited to the following embodiments, and may be carried out with modifications as appropriate within the spirit of the present invention.

The compound or the salt thereof obtained by the method of the present invention is represented b the following General Formula (1):

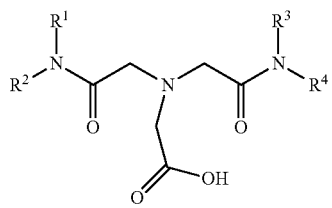

(1)

wherein in Formula (1), $R^1$, $R^2$, $R^3$, and $R^4$ independently represent the same or different hydrocarbon group, with the proviso that the total number of carbon atoms in the hydrocarbon groups $R^1$, $R^2$, $R^3$, and $R^4$ is 8 to 64.

The "salt thereof" means a salt formed by the compound represented by General Formula (1) and an inn or the like, and the type of the ion for the formation of the salt is not limited.

Examples of the type of the salt formed from the compound represented by General Formula (1) include, but not limited to, ammonium salt, lithium salt, sodium salt, potassium salt, hydrochloric acid salt, nitric acid salt, sulfuric acid salt, and acetic acid salt.

$R^1$, $R^2$, $R^3$, and $R^4$ each represent the same or different hydrocarbon group. The "hydrocarbon group" means a hydrocarbon group that is not limited to linear saturated hydrocarbon groups, and may contain each of a carbon-carbon unsaturated bond, branched structure, and cyclic structure.

The total number of carbon atoms in the hydrocarbon groups $R^1$, $R^2$, $R^3$, and $R^4$ is 8 to 64. The total number is preferably not less than 16, more preferably not less than 24, and preferably not more than 56, more preferably not more than 48.

The number of carbon atoms in each of the hydrocarbon groups $R^1$, $R^2$, $R^3$, and $R^4$ is usually not less than 2, preferably not less than 4, more preferably not less than 6, and usually not more than 16, preferably not more than 14, more preferably not more than 12.

Examples of $R^1$, $R^2$, $R^3$, and $R^4$ include an ethyl group ($-C_2H_5$), n-propyl group ($-^nC_3H_7$), i-propyl group ($-^iC_3H_7$), n-butyl group ($-^nC_4H_9$), t-butyl group ($-^tC_4H_9$), n-pentyl group ($-^nC_5H_{11}$), n-hexyl group ($-^nC_6H_{13}$), n-heptyl group ($-^nC_7H_{15}$), n-octyl group ($-^nC_8H_{17}$), 2-ethylhexyl group ($-CH_2CH(C_2H_5)C_4H_9$), n-nonyl group ($-^nC_9H_{19}$), n-decyl group ($-^nC_{10}H_{21}$), n-undecyl group ($-^nC_{11}H_{23}$), n-dodecyl group ($-^nC_{12}H_{25}$), n-tridecyl group ($-^nC_{13}H_{27}$), n-tetradecyl group ($-^nC_{14}H_{29}$), n-pentadecyl group ($-^nC_{15}H_{31}$), n-hexadecyl group ($-^nC_{16}H_{33}$), cyclohexyl group ($-^cC_6H_{11}$), phenyl group ($-C_6H_6$), and naphthyl group ($-C_{10}H_7$). Among these, an n-hexyl group ($-^nC_6H^{13}$), n-octyl group ($-^nC_8H_{17}$), 2-diethylhexyl group ($-CH_2CH(C_2H_5)C_4H_9$), n-decyl group ($-^nC_{10}H_{21}$), n-dodecyl group ($-^nC_{12}H_{25}$), and the like are preferred.

Examples of the compound of General Formula (1) include those represented by the allowing Formulae.

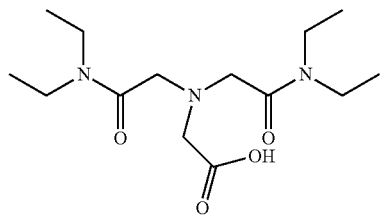

-continued

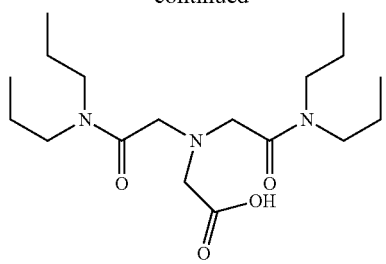

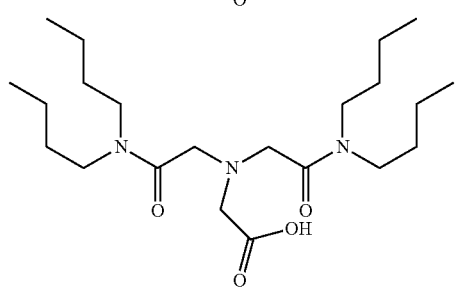

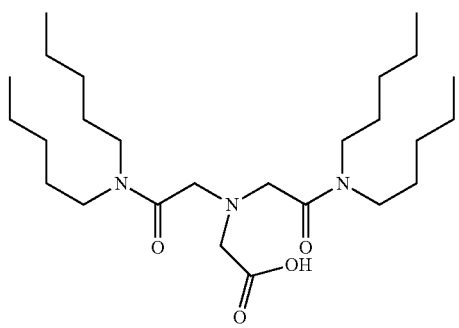

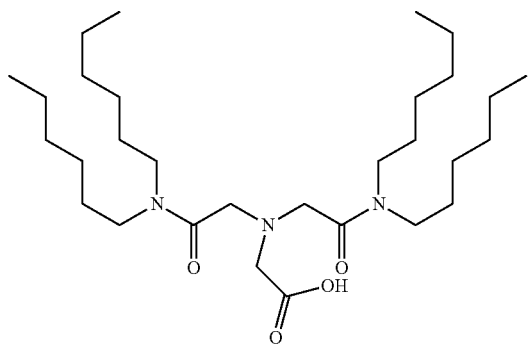

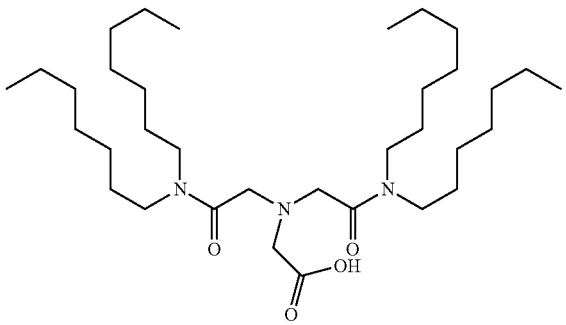

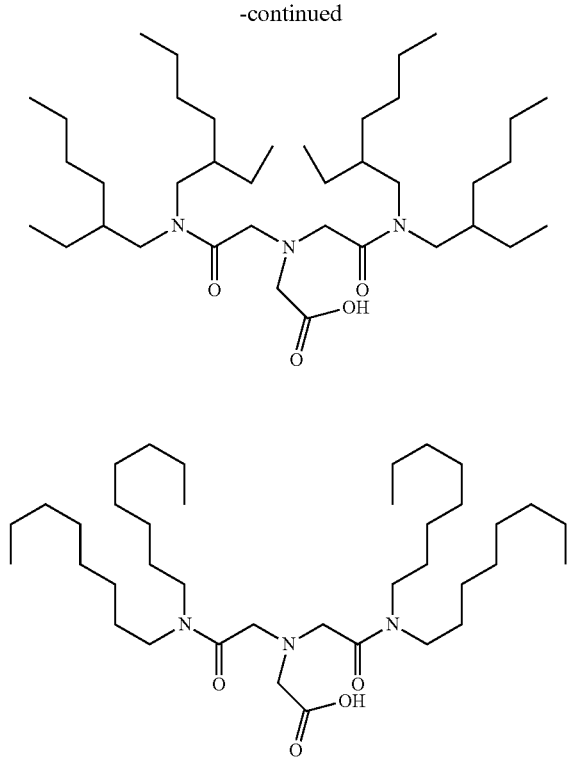

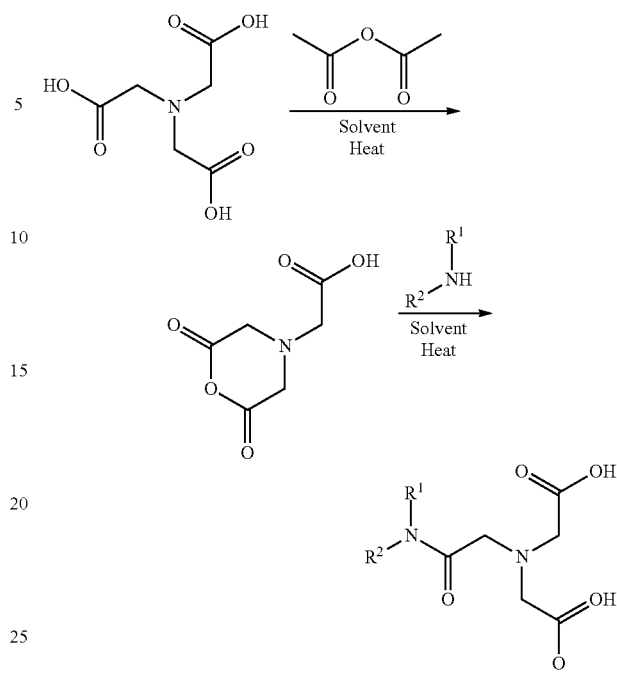

(II) A step of dehydrating the nitrilotriacetic acid derivative to obtain a nitrilotriacetic acid derivative anhydride, and reacting the nitrilotriacetic acid derivative anhydride with a dialkylamine $NHR^3R^4$ to allow amidation of one carboxyl group with the dialkylamine to obtain a tetraalkylnitriloacetic acid diacetamide.

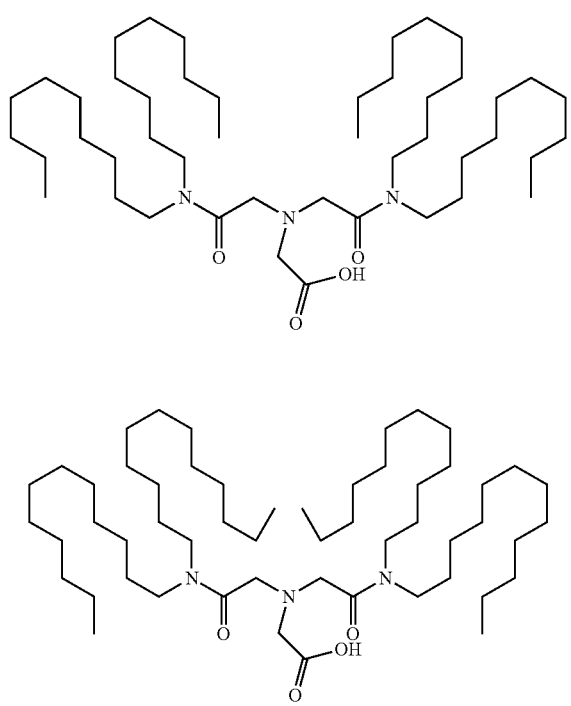

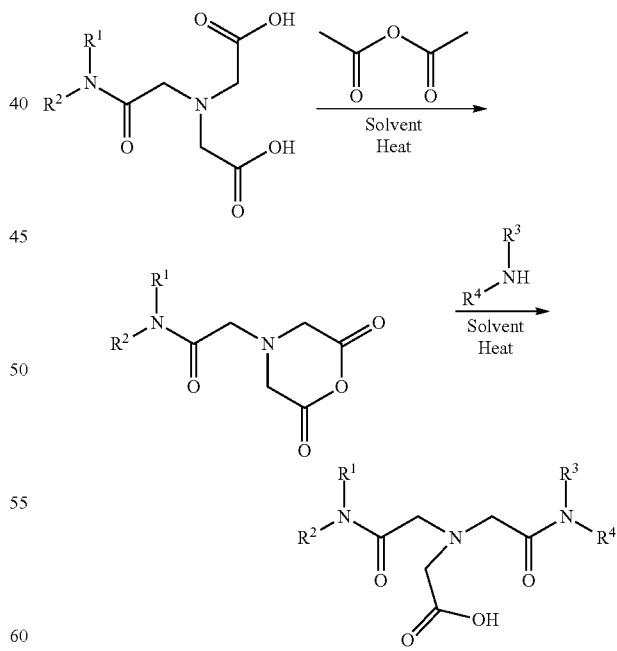

The production method of the present invention includes the following Steps (I) and (II).

(I) A step of dehydrating nitrilotriacetic acid to obtain nitrilotriacetic acid anhydride, and reacting the nitrilotriacetic acid anhydride with a dialkylamine $NHR^1R^2$ to allow nucleophilic substitution reaction of the dialkylamine to obtain a nitrilotriacetic acid derivative.

The types of the dialkylamine $NHR^1R^2$ and dialkylamine $NHR^3R^4$ may be appropriately selected depending on $R^1R^2$, $R^3$, and $R^4$ in General Formula (1). Examples of the types of the dialkylamines include the compounds represented by the following formulae.

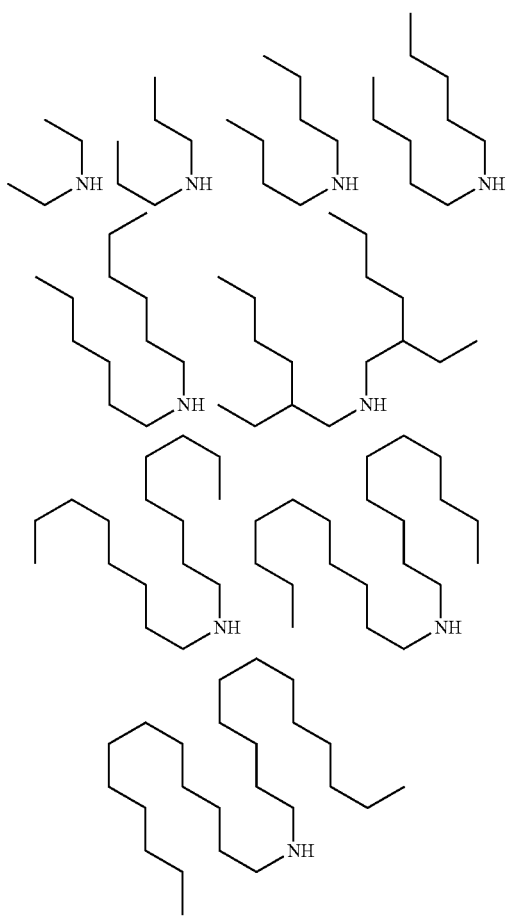

These compounds may be commercially available, or may be synthesized. By selecting the types of the dialkylamines, a wide range of compounds corresponding to General Formula (1) can be produced.

Step (I)

In Step (I), nitrilotriacetic acid (i) as a raw material is reacted with a dehydrating agent to allow dehydration, and thereafter, preferably, unreacted dehydrating agent, its reaction residue (the reaction solvent, and hydrolysate of the dehydrating agent produced by the reaction), and the like are evaporated under reduced pressure, followed by reacting the resulting nitrilotriacetic acid anhydride (ii) with a dialkylamine ($NHR^1R^2$) to obtain a nitrilotriacetic acid derivative (iii).

The dehydration reaction in Step (I) is preferably carried out at a reaction temperature of not less than room temperature for a reaction time of not less than 1 hour.

The higher the reaction temperature is, the higher the reaction rate is. However, a high reaction temperature is likely to cause production of by-products. In practice, a high reaction temperature may cause a change in the color of the reaction solution to brown or, in extreme cases, to black. Thus, the reaction temperature is preferably from room temperature (for example, 20° C.) to 40° C.

In cases where the reaction time is less than 1 hour, the rate of reaction does not reach a sufficient level. Therefore, the reaction time is preferably 1 to 6 hours, more preferably 2 to 5 hours.

The dehydrating agent is not limited as long as it is a dehydrating agent capable of converting nitrilotriacetic acid (i) to nitrilotriacetic acid anhydride (ii) by dehydration. The dehydrating agent is preferably a low boiling point dehydrating agent from the viewpoint of evaporating, under reduced pressure, unreacted dehydrating agent and hydrolysate of the dehydrating agent produced b the reaction, after the reaction using the dehydrating agent. Examples of the dehydrating agent include acetic anhydride, trichloroacetic anhydride, trifluoracetic anhydride, and mixtures of these. When this method is used, there is no need to remove the dehydrating agent by washing with water, and the synthesis process can therefore be simplified. That is, the subsequent synthesis process can be begun without purification. In cases where the dehydrating agent is remaining, it reacts with the dialkylamine used in the subsequent synthesis process. Thus, the dehydrating agent is preferably completely evaporated under reduced pressure.

In cases where the dehydrating agent is used in a large excess amount relative to nitrilotriacetic acid (i), the reaction can be allowed to proceed more easily, but the evaporation under reduced pressure takes a longer time in such cases. On the other hand, in cases where the amount of the dehydrating agent is about equal to the amount of nitrilotriacetic acid (i), the reaction is less likely to proceed. Thus, the amount of the dehydrating agent is preferably 2 to 6 equivalents, more preferably 3 to 5 equivalents with respect to nitrilotriacetic acid (i).

The reaction solvent is not limited as long as it is a solvent in which nitrilotriacetic acid (i) and the dehydrating agent can be dissolved. The reaction Solvent is preferably a low boiling point solvent. Examples of the reaction solvent include pyridine, dimethylformamide (DMF), and dimethylacetamide and mixtures of these. Among these, pyridine is more preferred since it also functions as a catalyst for the dehydration reaction.

The temperature for the evaporation under reduced pressure may be set depending on the degree of vacuum. As the temperature increases, by-products become more likely to be produced, which may lead to a change in the color of the product to brown or, in extreme cases, to black. Thus, the evaporation under reduced pressure is preferably carried out with a sufficient degree of vacuum at a temperature that is as low as possible (for example, 50 to 70° C.).

The nucleophilic substitution reaction with the dialkylamine in Step (I) is preferably carried out at a reaction temperature of not less than room temperature for a reaction time of not less than 8 hours.

The higher the reaction temperature is, the higher the reaction rate is. However, a high reaction temperature is likely to cause production of by-products Thus, the reaction temperature is preferably from room temperature (for example, 20° C.) to 50° C.

In cases where the reaction time is less than 5 hours, the rate of reaction does not reach a sufficient level. Therefore, the reaction time is preferably 8 to 20 hours, more preferably 10 to 18 hours.

The amount of the dialkylamine is preferably not less than 1.0 equivalent, more preferably 1.0 to 1.1 equivalents with respect to the nitrilotriacetic acid anhydride (ii) obtained in Step (I). In cases where the amount is less than 1.0 equivalent, considerable amounts of unreacted nitrilotriacetic acid anhydride (ii) and its hydrolysate nitrilotriacetic acid (i) remain. Therefore, in cases where the final product is used as a metal extractant, inhibition of extraction occurs in solvent extraction since the metal extractant used therefor contains the residual nitrilotriacetic acid anhydride and nitrilotriacetic acid (i). This may lead to insufficient extraction separation performance, which problematic. On the other hand, in cases where the amount exceeds 1.1 equivalents, unreacted dialkylamine remains. Although dialkylamine does not affect the solvent extraction in some cases, its use in an excessive amount is meaningless, and increases the cost for the synthesis raw material. Thus, the amount is preferably not more than 1.1 equivalents.

The reaction solvent is not limited as long as it is a solvent in which the nitrilotriacetic acid anhydride (ii) produced from the nitrilotriacetic acid (i), and the dialkylamine, can be dissolved, and which does not inhibit the reaction. Examples of the reaction solvent include pyridine, dimethylformamide (DMF), and dimethylacetamide. DMF is more preferred.

In cases where a highly pure product is demanded, purification can be carried out by neutralization reaction with an acid or a base, or by reprecipitation using a poor solvent such as acetone. On the other hand, in cases where the cost is to be reduced, or where impurities do not affect the solvent extraction, the purification process may be omitted.

Step (II)

In Step (II), the nitrilotriacetic acid derivative (iii) obtained in Step (I) is reacted with a dehydrating agent similarly to Step (I) as described above to allow dehydration, and thereafter, preferably, unreacted dehydrating agent, its reaction residue (the reaction solvent, and hydrolysate of the dehydrating agent produced by the reaction), and the like are evaporated under reduced pressure, followed by reacting the resulting nitrilotriacetic acid derivative anhydride (iv) with a dialkylamine $NHR^3R^4$ to obtain tetraalkylnitriloacetic acid diacetamide compound (1).

The dehydration reaction in Step (II) is preferably carried out at a reaction temperature of not less than room temperature for a reaction time of not less than 1 hour.

The higher the reaction temperature is, the higher the reaction rate is. However, a high reaction temperature is likely to cause production of by-products. Thus, the reaction temperature is preferably from room temperature (for example, 20° C.) to 40° C.

In cases where the reaction time is less than 1 hour, the rate of reaction does not reach a sufficient level. Therefore, the reaction time is preferably not less than 1 hour.

The dehydrating agent is not limited as long as it is a dehydrating agent capable of converting the nitrilotriacetic acid derivative (iii) to the nitrilotriacetic acid derivative anhydride (iv) by dehydration. The dehydrating agent is preferably a low boiling point dehydrating agent from the viewpoint of evaporating, under reduced pressure, unreacted dehydrating agent and hydrolysate of the dehydrating agent produced by the reaction, after the reaction using the dehydrating agent. Examples of the dehydrating agent include acetic anhydride, trichloroacetic anhydride, trifluoroacetic anhydride, and mixtures of these. When this method is used, there is no need to remove the dehydrating agent by washing with water, and the synthesis process can therefore be simplified. That is, the subsequent synthesis process can be begun without purification. In cases where the dehydrating agent is remaining, it reacts with the dialkylamine used in the subsequent synthesis process. Thus, the dehydrating agent is preferably completely evaporated under reduced pressure.

In cases where the dehydrating agent is used in a large excess amount relative to the nitrilotriacetic acid derivative (iii) obtained in Step (I), the reaction can be allowed to proceed more easily, but the evaporation under reduced pressure takes a longer time in such cases. On the other hand, in cases where the amount of the dehydrating agent is about equal to the amount of the nitrilotriacetic acid derivative (iii), the reaction is less likely to proceed. Thus, the amount of the dehydrating agent preferably 2 to 6 equivalents, more preferably 3 to 5 equivalents with respect to the nitrilotriacetic acid derivative (iii).

The reaction solvent is not limited as long as it is a solvent in which the nitrilotriacetic acid derivative (iii) and the dehydrating agent can be dissolved. The reaction solvent is preferably a low boiling point solvent. Examples of the reaction solvent include pyridine, dimethylformamide (DMF), and dimethylacetamide, and mixtures of these. Among these, pyridine is more preferred, since it also functions as a catalyst for the dehydration reaction.

The temperature for the evaporation under reduced pressure may be set depending on the degree of vacuum. As the temperature is by-products become more likely to be produced. Thus, the evaporation under reduced pressure is preferably carried out with a sufficient degree of vacuum at a temperature that is as low as possible (for example, 50 to 70° C.), The nucleophilic substitution reaction with the dialkylamine in Step (II) preferably carried out at a reaction temperature of not less than room temperature for a reaction time of not less than 8 hours.

The higher the reaction temperature is, the higher the reaction rate is. However, a high reaction temperature is likely to cause production of by-products. Thus, the reaction temperature is preferably from room temperature (for example, 20° C.) to 50° C.

In cases where the reaction time is less than 5 hours, the rate of reaction does not reach a sufficient level. Therefore, the reaction time is preferably 8 to 20 hours, more preferably 10 to 18 hours.

The amount of the dialkylamine is preferably not less than 1.0 equivalent, more preferably 1.0 to 1.1 equivalents with respect to the nitrilotriacetic acid derivative anhydride (iv) obtained in Step (II). In cases where the amount is less than 1.0 equivalent, considerable amounts of unreacted nitrilotriacetic acid derivative anhydride (iv) and its hydrolysate nitrilotriacetic acid derivative (iii) remain. Therefore, in cases here the final product is used as a metal extractant, solvent extraction may be adversely affected to cause a decrease in the extraction efficiency and the like since the metal extractant used for the solvent extraction contains the residual nitrilotriacetic acid derivative anhydride (iv) and the nitrilotriacetic acid derivative (iii). On the other hand, in cases where the amount exceeds 1.1 equivalents, unreacted dialkylamine remains. Although dialkylamine does not affect the solvent extraction in some cases, its use in an excessive amount is meaningless, and increases the cost for the synthesis raw material. Thus, the amount is preferably not more than 1.1 equivalents.

The reaction solvent is not limited as long as it is a solvent in which the nitrilotriacetic acid derivative anhydride (iv) produced from the nitrilotriacetic acid derivative (iii), and the dialkylamine, can be dissolved, and which does not inhibit the reaction. Examples of the reaction solvent include pyridine, dimethylformamide (DMF), and dimethylacetamide. DMF is more preferred.

In cases where the nitrilotriacetic acid derivative anhydride (iv) and the dialkylamine are soluble in the organic solvent used for the solvent extraction of a metal using the tetraalkylnitriloacetic acid diacetamide, this organic solvent can be used as the reaction solvent. In such cases, the solution containing the metal extractant obtained after the reaction may be used as an organic phase for the solvent extraction as it is or after adjusting the metal extractant concentration to a predetermined level. On the other hand, in cases where the reaction medium is water-soluble, the reaction medium needs to be evaporated under reduced pressure after the reaction.

In cases where a highly pure product is demanded, the product may be dissolved in the organic solvent used for the solvent extraction, and may then be washed using an acid or water. Thereafter, the solution containing the metal extractant (tetraalkylnitriloacetic acid diacetamide) may be used as an organic phase for the solvent extraction as it is or after adjusting the metal extractant concentration to a predetermined level. In cases where the cost is to be reduced, or where impurities do not affect the solvent extraction, the purification process may be omitted.

EXAMPLES

The present invention is described below more concretely by referring to Examples. However, the present invention may be modified as appropriate within the spirit of the present invention. Accordingly, the scope of the present invention should not be interpreted as being limited to the following specific examples.

Example 1; Synthesis of Tetraoctylnitriloacetic Acid Diacetamide (TONTADA)

By the reaction represented by the following reaction equation, 2,2'-(2-dioctylamino)-2-oxoethylazanediyl) diacetic acid (which may be hereinafter simply referred to as "DONTAMA") was synthesized.

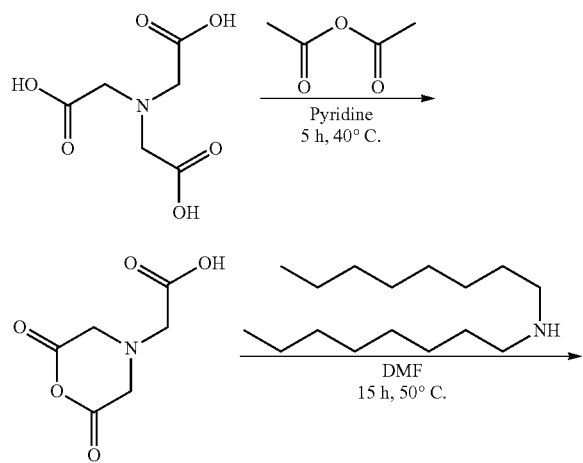

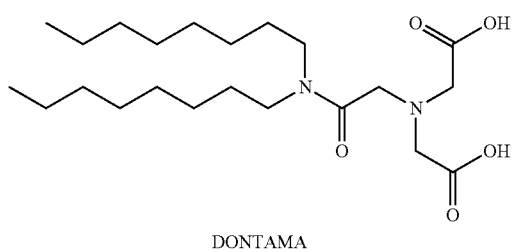

DONTAMA

With 9.75 g (0.05 mol) of nitrilotriacetic acid, 30 mL (0.37 mol) of pyridine as a solvent and 20.6 g (0.2 mol) of acetic anhydride as a dehydrating agent were mixed, and reaction was carried out at 40° C. for 5 hours. Thereafter, the mixture was heated to 60° C., and excessive acetic anhydride and pyridine, and acetic acid produced by the reaction were evaporated under reduced pressure. To the resulting nitrilotriacetic acid anhydride, 50 mL of dimethylformamide (DMF) was added. After allowing complete dissolution, 12.32 g (0.05 mol) of dioctylamine was added, and reaction was carried out at 50° C. for 15 hours. Thereafter, the mixture was heated to 75° C., and the solvent as evaporated under reduced pressure. To the resulting product, 130 mL of water and 20 mL of 5 mol/L aqueous sodium hydroxide solution (OH$^-$, 0.1 mol.) were added. After allowing complete dissolution, 37 mL of 3 mol/L hydrochloric acid (H$^+$, 0.111 mol) was added with stirring at room temperature, and the precipitate produced was collected by filtration. Washing was carried out with 100 mL of water to remove excessive acid. Subsequently, 100 mL of acetone was added, and the product was then allowed to be dissolved completely by heating. The resulting solution was then cooled to allow reprecipitation of the product, and the product was collected by filtration. As a result of identification of the resulting white powder using the nuclear magnetic resonance method (NMR), it was found to be 2,2'-2-(dioctylamino)-2-oxoethylazanediyl) diacetic acid (DONTAMA).

By the reaction represented by the following reaction equation, tetraoctylnitriloacetic acid diacetamide (which may be hereinafter simply referred to "TONTADA") was synthesized.

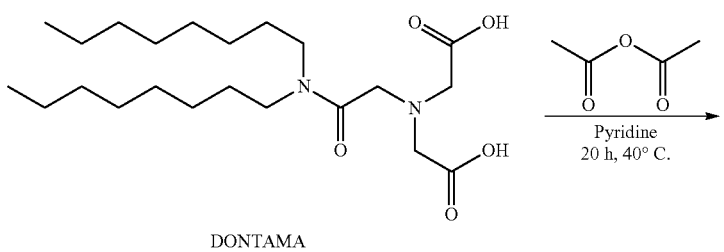

DONTAMA

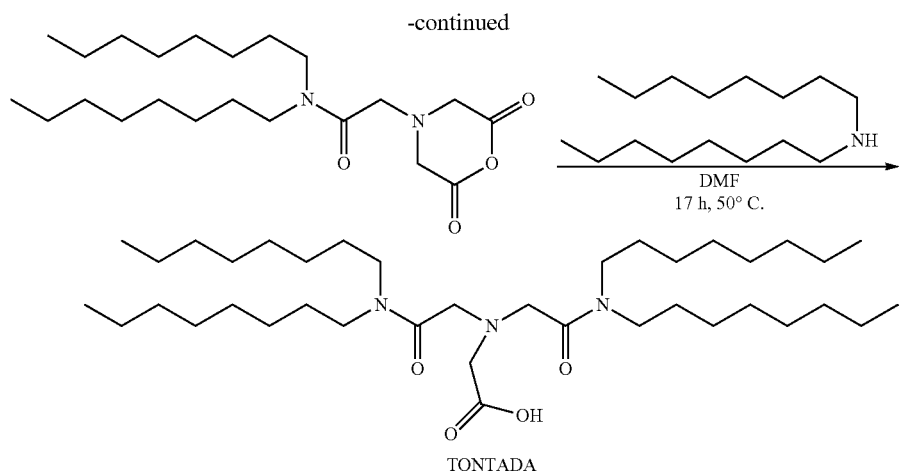

TONTADA

With 4.2 g 0.01 mol) of the synthesized DONTAMA, 6 mL (0.075 mol) of pyridine as a solvent and 4.1 g (0.04 mol) of acetic anhydride as a dehydrating agent were mixed, and reaction was carried out at 40° C. for 20 hours. Thereafter, the mixture was heated to 70° C., and excessive acetic anhydride and pyridine, and acetic acid produced by the reaction were evaporated under reduced pressure. To the resulting anhydride of DONTAMA, 15 mL of dimethylformamide (DMF) was added. After allowing complete dissolution, 2.5 g (0.01 mol) of dioctylamine was added, and reaction was carried out at 50° C. for 17 hours. Thereafter, the mixture was heated to 75° C., and the solvent was evaporated under reduced pressure. After redissolving the resulting product in an appropriate organic solvent, separation was carried out three times with 100 mL of 1 mol/L hydrochloric acid and three times with 100 mL of ultrapure water, and then the solvent was completely evaporated under reduced pressure. As a result of identification of the resulting synthesis product using the nuclear magnetic resonance method (NMR), it was found to be tetraoctylnitriloacetic acid diacetamide (TONTADA). The result of $^1$H NMR is shown in the drawing.

$^1$H NMR (400 MHz, CDCl$_3$, 25° C.): δ0.88 (m, 12H, CH$_3$), 1.27 (s, 40H, CH$_3$(CH$_2$)$_5$), 1.52 (8H, CH$_2$CH$_2$N), 3.10 (t, 4H, CH$_2$N), 3.30 (t, 4H, CH$_2$N), 3.48 (s, 2H, NCH$_2$COOH), 3.68 (s, 4H, NCH$_2$C=O).

INDUSTRIAL APPLICABILITY

According to the present invention, an extractant for extraction of a valuable metal such as a rare metal or a noble metal, or of a highly toxic, harmful metal, can be simply, safely, and inexpensively synthesized without use of a hazardous chemical or an expensive chemical. The present invention is therefore industrially highly useful.

While the invention has been described in detail with reference to exemplary embodiments thereof, it will be apparent to one skilled in the art that various changes may be made, and equivalents employed, without departing from the scope of the invention. Each of the aforementioned documents as well as JP2017-182484 is incorporated by reference herein in its entirety.

What is claimed is:
1. A method for synthesizing a compound represented by the General Formula (1):

(1)

$$R^2\text{-}N(R^1)\text{-}C(=O)\text{-}CH_2\text{-}N(CH_2COOH)\text{-}CH_2\text{-}C(=O)\text{-}N(R^3)\text{-}R^4$$

wherein in Formula (1), R$^1$, R$^2$, R$^3$, and R$^4$ independently represent the same or different hydrocarbon group, with the proviso that the total number of carbon atoms in the hydrocarbon groups R$^1$, R$^2$, R$^3$, and R$^4$ is 8 to 64, the method comprising the following Steps (I) and (II):

Step (I): dehydrating nitrilotriacetic acid (i) to obtain nitrilotriacetic acid anhydride (ii), and reacting the nitrilotriacetic acid anhydride (ii) with a dialkylamine NHR$^1$R$^2$ to obtain a nitrilotriacetic acid derivative (iii);

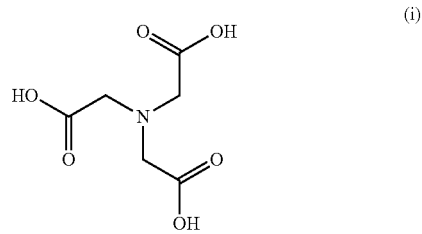

(i)

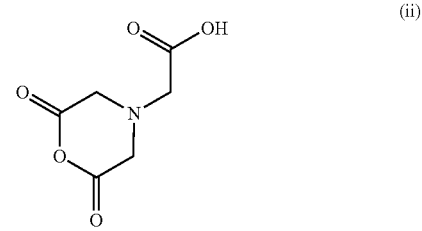

(ii)

-continued

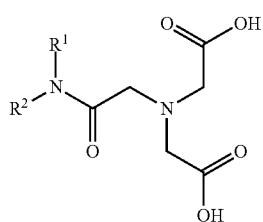

and

Step (II): dehydrating the nitrilotriacetic acid derivative (iii) to obtain a nitrilotriacetic acid derivative anhydride (iv), and reacting the nitrilotriacetic acid derivative anhydride (iv) with a dialkylamine NHR³R⁴ to obtain the compound represented by General Formula (1).

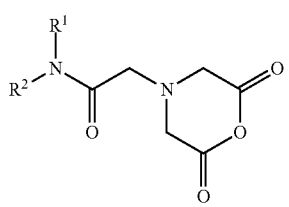

2. The method according to claim 1, wherein the dehydrating agent used in Step (I) and Step (II) is selected from the group consisting of acetic anhydride, trichloroacetic anhydride, trifluoroacetic anhydride, and a mixture thereof.

3. The method according to claim 1, wherein in Step (I) and Step (II), dehydration is performed by reacting 2 to 6 equivalents of a dehydrating agent with the nitrilotriacetic acid (i) and/or the nitrilotriacetic acid derivative (iii).

4. The method according to claim 1, wherein in Step (I) and Step (II), after the dehydration of nitrilotriacetic acid (i) and/or the nitrilotriacetic acid derivative (iii), an operation of evaporation of unreacted dehydrating agent under reduced pressure is performed.

5. The method according to claim 1, wherein in Step (I) and Step (II), a solvent used for the dehydration reaction of nitrilotriacetic acid (i) and/or the nitrilotriacetic acid derivative (iii) is selected from the group consisting of pyridine, dimethylformamide, dimethylacetamide, and a mixture thereof.

6. The method according to claim 1, wherein in Step (I) and Step (II), 1.0 to 1.1 equivalents of the dialkylamine is reacted with the nitrilotriacetic acid anhydride (ii) and/or the nitrilotriacetic acid derivative anhydride (iv).

7. The method according to claim 1, wherein the compound represented by General Formula (1) is selected from the following compounds

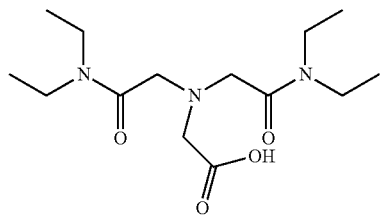

-continued

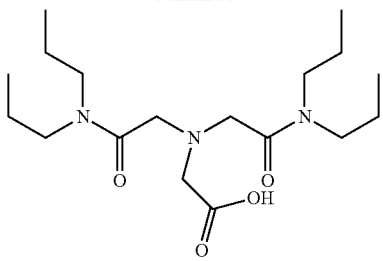

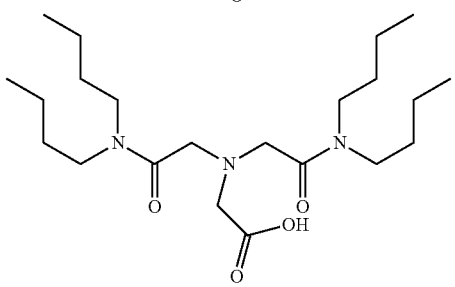

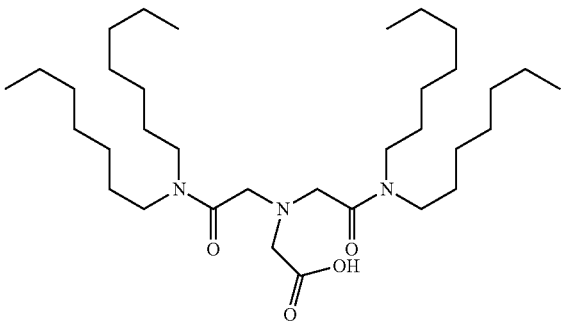

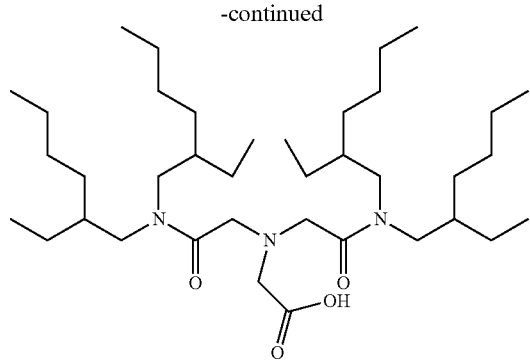

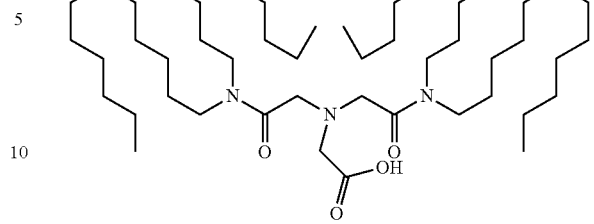

8. The method according to claim 1, wherein the compound represented by General Formula (1) is tetraoctylnitriloacetic acid diacetamide.

9. The method according to claim 1, wherein in Step (I) and Step (II), a solvent used for the dehydration reaction of nitrilotriacetic acid (i) and the nitrilotriacetic acid derivative (iii) is selected from the group consisting of pyridine, dimethylformamide, and a mixture thereof.

10. The method according to claim 1, wherein in Step (I) and Step (II), a solvent used for the dehydration reaction of nitrilotriacetic acid (i) and the nitrilotriacetic acid derivative (iii) is pyridine.

11. The method according to claim 1, wherein in Step (I) and Step (II), a solvent used for the reaction of nitrilotriacetic acid anhydride (ii) and the nitrilotriacetic acid derivative anhydride (iv) with the dialkylamine is selected from the group consisting of pyridine, dimethylformamide, dimethylacetamide, and a mixture thereof.

12. The method according to claim 1, wherein in Step (I) and Step (II), a solvent used for the reaction of nitrilotriacetic acid anhydride (ii) and the nitrilotriacetic acid derivative anhydride (iv) with the dialkylamine is dimethylformamide.

* * * * *